US00PP22955P2

(12) United States Plant Patent
Bergman

(10) Patent No.: US PP22,955 P2
(45) Date of Patent: Aug. 14, 2012

(54) ***CHRYSANTHEMUM* PLANT NAMED 'CIDZ0006'**

(50) Latin Name: *Chrysanthemum×morifolium*
Varietal Denomination: CIDZ0006

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,100

(22) Filed: Jul. 22, 2011

(51) Int. Cl.
*A01H 5/00* (2006.01)

(52) U.S. Cl. ..... Plt./286

(58) Field of Classification Search ..... Plt./286
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0006' particularly distinguished by daisy-shaped inflorescences, iridescent red-purple ray floret color with a spot of yellow and green basally with a slow maturing hint of green on the un-opened disc florets, yellow buds in lower light levels or yellow-orange buds in high light conditions, medium green foliage, vigorous growth habit, and 8½ week flowering response.

1 Drawing Sheet

Latin name of the genus and species of the plant claimed: *Chrysanthemum×morifolium.*

Varietal denomination: 'CIDZ0006'.

BACKGROUND OF THE NEW PLANT

The present invention comprises a new *Chrysanthemum*, botanically known as *Chrysanthemum×morifolium*, and hereinafter referred to by the variety name 'CIDZ0006'.

'CIDZ0006' is a product of a planned breeding program. The new cultivar has daisy-shaped inflorescences, iridescent red-purple ray floret color with a spot of yellow and green basally with a slow maturing hint of green on the un-opened disc florets, yellow buds in lower light levels or yellow-orange buds in high light conditions, medium green foliage, vigorous growth habit, and 8½ week flowering response.

'CIDZ0006' originated from a hybridization made in April 2006 in a controlled breeding environment in Salinas, Calif., USA. The female parent was the proprietary plant designated 'YB-A3383', unpatented, with bronze ray floret color and smaller flower size.

The male parent of 'CIDZ0006' was a proprietary, unpatented plant identified as 'YB-A7784' with salmon pink ray floret color, a lighter green disc color, and produces pollen.

'CIDZ0006' was selected as one flowering plant within the progeny of the stated cross in November 2006 in a controlled environment in Fort Myers, Fla., USA.

The first act of asexual reproduction of 'CIDZ0006' was accomplished when vegetative cuttings were propagated from the initial selection in February 2007 in a controlled environment in Fort Myers, Fla., USA.

BRIEF SUMMARY OF INVENTION

Horticultural examination of plants grown from cuttings of the plant initiated in February 2007, and continuing thereafter, has demonstrated that the combination of characteristics as herein disclosed for 'CIDZ0006' are firmly fixed and are retained through successive generations of asexual reproduction.

'CIDZ0006' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7064). 'CIDZ0006' has not been made publicly available more than -one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0006' with colors being as true as possible with an illustration of this type.

Figure 1:
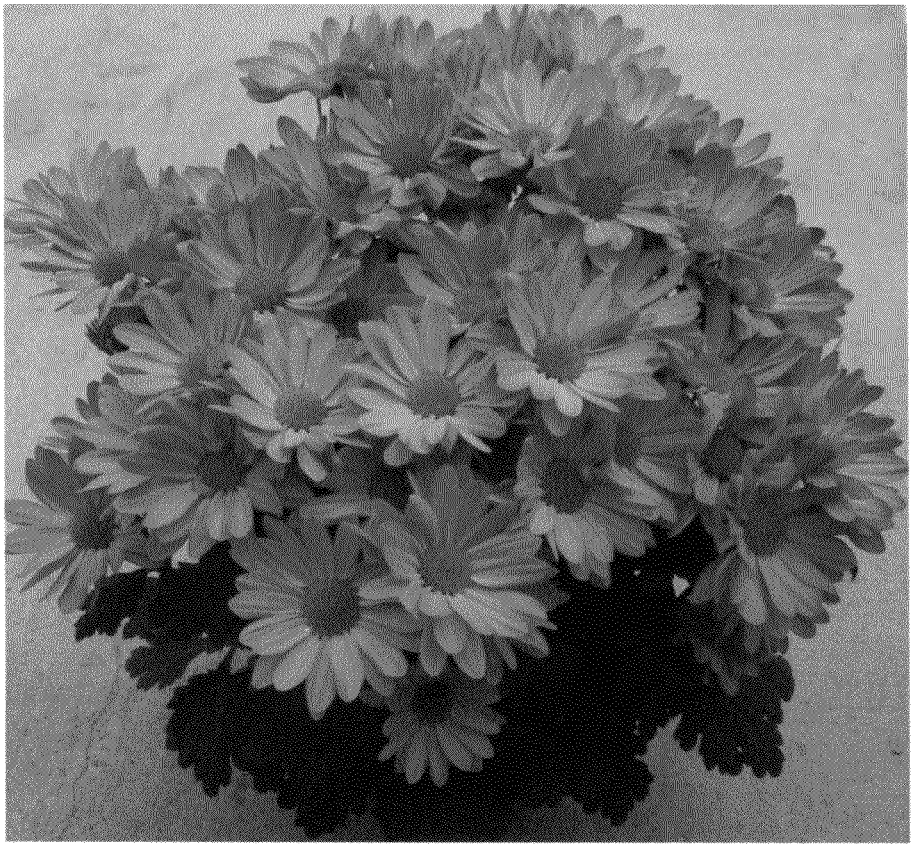
Figure 2:
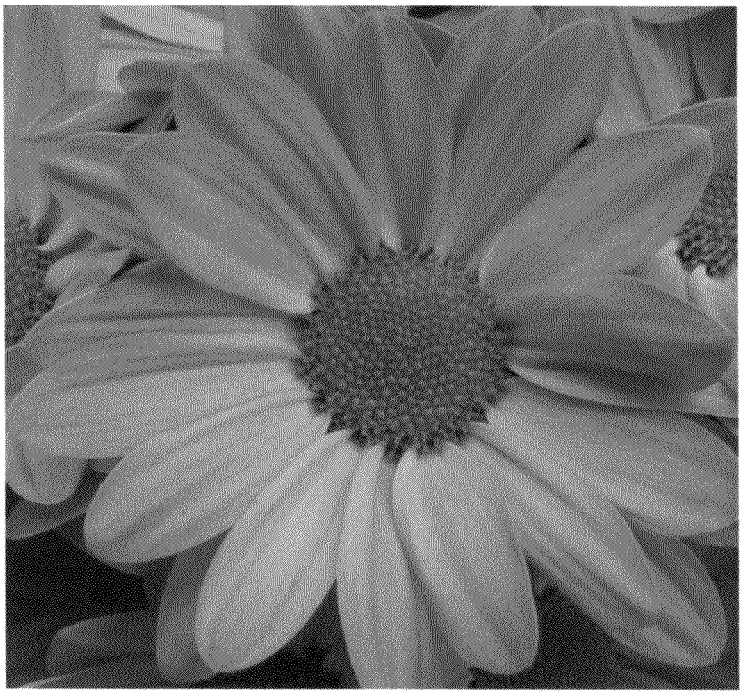

The photographic drawing shows in FIG. 1 four flowering potted plants of the new variety and in FIG. 2 a close-up of the inflorescences.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a five inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0006' AND A SIMILAR VARIETY

| | 'CIDZ0006' | 'Yoeugene' (U.S. Plant Pat. No. 11,917) |
|---|---|---|
| Ray floret color: | More intense | Less intense |
| Quantity of ray florets: | About 25-33 | About 22 |
| Vigor: | More vigorous growth | Less vigorous growth |
| Quantity of disc florets | About 280+ | About 177 |

Plant:

*Form, growth and habit*.—Herbaceous pot-type, stems upright, freely branching, strong and moderately vigorous growth habit.

*Plant height*.—23-26.0 cm.

*Plant height* (*inflorescence included*).—34-36.0 cm.

*Plant width*.—14-16.0 cm.

Roots:

*Number of days to initiate roots*.—About 4 days at about 22 degrees C.

*Number of days to produce a rooted cutting*.—About 10 days at 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 137A but darker.

*Lower surface*.—RHS 137C.

*Mature, leaf color, upper surface*.—RHS 137A but darker.

*Lower surface*.—RHS 137C.

*Length*.—8.0-9.0 cm.

*Width*.—5.7-6.4 cm.

*Shape*.—Ovate.

*Base shape*.—Attenuate.

*Apex shape*.—Mucronulate.

*Margin*.—Palmately lobed; irregularly serrate.

*Texture, upper surface*.—Bifid T-shaped hairs.

*Lower surface*.—Bifid T-shaped hairs.

*Color of veins, upper surface*.—RHS 144A.

*Color of veins, lower surface*.—RHS 144A.

*Petiole color*.—RHS 144A.

*Length*.—2.5-3.0 cm.

*Diameter*.—0.35-0.4 cm.

*Texture*.—Bifid T-shaped hairs.

Stem:

*Quantity of main branches per plant*.—3-4.

*Color of stem*.—RHS 137B but appears lighter due to hairs.

*Length of stem*.—20-23.0 cm.

*Diameter*.—0.5-0.6 cm.

*Length of internodes*.—1.5-3.0 cm.

*Texture*.—Bifid T-shaped hairs.

*Color of peduncle*.—RHS 137B but appears lighter due to hairs.

*Length of peduncle*.—10.0-10.5 cm.

*Peduncle diameter*.—0.3-0.4 cm.

*Texture*.—Bifid T-shaped hairs.

Inflorescence:

*Type*.—Compositae type, solitary inflorescences, daisy-type, borne terminally above foliage, ray florets arranged acropetally on a capitulum.

*Quantity of short days to flowering* (*response time*).—About 8.5 weeks.

*Quantity of inflorescences per plant*.—25-30.

*Lastingness of individual blooms on the plant*.—About 4 weeks.

*Fragrance*.—Slightly spicy.

Bud (just when opening/showing color):

*Color*.—RHS 3B basally, RHS 1B towards the apex.

*Length*.—1.3-1.6 cm.

*Width*.—1.5 cm.

*Shape*.—Oblate.

Immature inflorescence:

*Diameter*.—5.0-6.5 cm.

*Color of ray florets, upper surface*.—RHS 70B ground color becoming closer to RHS 70C basally, with lightly overlaid in a slight mottled pattern with RHS 70A distally, with a spot of RHS 154C overlaid with a spot RHS 145A to RHS 145B at the very base of the floret.

*Lower surface*.—RHS N155C to RHS 155D, heavily overlaid with light speckles of RHS 180 D and margins of slight hue RHS 185D.

Mature inflorescence:

*Diameter*.—8.0-8.5 cm.

*Depth*.—2.0 cm.

*Total diameter of 'disc'*.—2.0 cm.

*Receptacle height*.—0.6-0.7 cm.

*Receptacle diameter*.—1.0 cm.

Ray florets:

*Average quantity of florets*.—25-33 in two whorls.

*Color of florets, upper surface*.—Closest to RHS 70C ground color, lightly overlaid and mottled with darker tones especially distally, and with a spot of RHS 154C to RHS 154D overlaid with a spot RHS 145B at the very base that forms a halo around the 'disc'.

*Lower surface*.—Closest to RHS 155D, overlaid with light speckles of RHS 180D and margins of slight hue RHS 185D.

*Length*.—3.5-3.8 cm.

*Width*.—1.0-1.3 cm.

*Shape*.—Elliptical.

*Apex shape*.—Slightly retuse.

*Margin*.—Entire.

*Texture, upper surface*.—Papillose.

*Lower surface*.—Papillose.

Disc florets:

*Average quantity of florets*.—280-300.

*Color of florets*.—Closest to RHS 13C that fades to RHS 20A at the apex with a hint of green on the un-opened disc florets that is closest to RHS 145B.

*Length*.—0.5-0.6 cm.

*Width*.—0.1 cm.

*Shape*.—Tubular, elongated.

*Apex shape*.—Acute, 5 pointed.

Phyllaries:

*Quantity*.—Approximately 30.

*Color, upper surface*.—RHS 137C.

*Lower surface*.—RHS 137B.

*Length*.—0.6-1.0 cm.

*Width*.—0.1-0.25 cm.

*Shape*.—Lanceolate.

*Apex shape*.—Acute.

*Base*.—Fused.

*Margins*.—Entire; papery.

*Texture, upper surface*.—Glabrous.
*Lower surface*.—Bifid T-shaped hairs.

Reproductive organs:

*Pistil*.—1.
*Found on both florets*.—Yes.
*Length*.—0.5-0.6 cm.
*Style color*.—RHS 1C but greener.
*Style length*.—0.4-0.5 cm.
*Stigma color*.—RHS 14A.
*Stigma shape*.—Bi-parted.
*Ovary color*.—Not observed.
*Stamens*.—1.
*Found on only disc florets*.—Yes.
*Color of filaments*.—RHS 1C but greener.
*Length filaments*.—0.3 cm.
*Anther color*.—RHS 13A.
*Anther length*.—0.1 cm.
*Anther shape*.—Oblong.
*Color of pollen*.—Not observed.
*Pollen amount*.—No pollen observed.
*Fertility/seed set*.—Has not been observed on this hybrid.

Disease/pest resistance: Disease/pest resistance as not been observed on this hybrid.

What is claimed is:

1. A new and distinct variety of *Chrysanthemum* plant named 'CIDZ0006' substantially as illustrated and described herein.

* * * * *